(12) United States Patent
Broom et al.

(10) Patent No.: US 10,470,755 B2
(45) Date of Patent: Nov. 12, 2019

(54) TISSUE FIXATION DEVICE

(71) Applicant: Covidien LP, Mansfield, MA (US)

(72) Inventors: Daniel Broom, Branford, CT (US); Joshua Stopek, Minneapolis, MN (US); Timothy Sargeant, Guilford, CT (US); Nicholas Maiorino, Branford, CT (US); Arpan Desai, Hamden, CT (US); Saumya Banerjee, Hamden, CT (US); Timothy Flavin, Evanston, IL (US)

(73) Assignee: Covidien LP, Mansfield, MA (US)

( * ) Notice: Subject to any disclaimer, the term of this patent is extended or adjusted under 35 U.S.C. 154(b) by 457 days.

(21) Appl. No.: 14/389,851

(22) PCT Filed: Nov. 18, 2013

(86) PCT No.: PCT/US2013/070470
§ 371 (c)(1),
(2) Date: Oct. 1, 2014

(87) PCT Pub. No.: WO2014/078754
PCT Pub. Date: May 22, 2014

(65) Prior Publication Data
US 2015/0039027 A1 Feb. 5, 2015

Related U.S. Application Data

(60) Provisional application No. 61/727,939, filed on Nov. 19, 2012.

(51) Int. Cl.
*A61B 17/04* (2006.01)
*A61B 17/064* (2006.01)
(Continued)

(52) U.S. Cl.
CPC .......... *A61B 17/04* (2013.01); *A61B 17/0401* (2013.01); *A61B 17/064* (2013.01);
(Continued)

(58) Field of Classification Search
None
See application file for complete search history.

(56) References Cited

U.S. PATENT DOCUMENTS 5,342,376 A     8/1994   Ruff
6,113,612 A *   9/2000   Swanson ............... A61F 2/88
                                                                                            623/1.15
(Continued)

FOREIGN PATENT DOCUMENTS

EP          2684527 A2    1/2014
KR      101132841 B1    4/2012
(Continued)

OTHER PUBLICATIONS

European Search Report EP13855719.4-1654 dated Apr. 16, 2016.
(Continued)

*Primary Examiner* — Shaun L David (57) ABSTRACT

A tissue fixation device includes an elongated body extending between a proximal portion and a distal portion including a plurality of barbed loops. The elongated body, proximal portion, and distal portion are provided in a variety of configurations depending upon the performance requirements desired of the tissue fixation device for the envisaged application of use.

20 Claims, 4 Drawing Sheets

(51) Int. Cl.
   *A61B 17/00* (2006.01)
   *A61B 17/06* (2006.01)
   *A61F 2/00* (2006.01)

(52) U.S. Cl.
   CPC ............... *A61B 2017/00004* (2013.01); *A61B 2017/00876* (2013.01); *A61B 2017/00893* (2013.01); *A61B 2017/042* (2013.01); *A61B 2017/0404* (2013.01); *A61B 2017/0406* (2013.01); *A61B 2017/0427* (2013.01); *A61B 2017/06176* (2013.01); *A61F 2/0063* (2013.01)

(56) References Cited

U.S. PATENT DOCUMENTS

| | | | |
|---|---|---|---|
| 6,599,310 B2 | 7/2003 | Leung et al. | |
| 2002/0156499 A1* | 10/2002 | Konya | A61B 17/12022 606/213 |
| 2006/0212055 A1* | 9/2006 | Karabey | A61B 17/12022 606/158 |
| 2008/0065203 A1* | 3/2008 | Khalapyan | A61F 2/2445 623/2.11 |
| 2009/0248066 A1 | 10/2009 | Wilkie | |
| 2011/0054522 A1 | 3/2011 | Lindh, Sr. et al. | |
| 2012/0116450 A1* | 5/2012 | McDevitt | A61B 17/0401 606/232 |
| 2012/0245629 A1 | 9/2012 | Gross et al. | |
| 2013/0345745 A1* | 12/2013 | Kim | A61B 17/06109 606/225 |
| 2015/0157309 A1* | 6/2015 | Bird | A61B 17/0401 606/232 |

FOREIGN PATENT DOCUMENTS

| | | |
|---|---|---|
| WO | 2003001979 | 1/2003 |
| WO | 2009013758 A2 | 1/2009 |
| WO | 2012/064902 A2 | 5/2012 |

OTHER PUBLICATIONS

International Search Report for PCT/US13/70470 date of completion is Jan. 22, 2014 (3 pages).

European Examination Report dated Sep. 21, 2017 issued in corresponding European Application No. 13855719.4.

\* cited by examiner

TISSUE FIXATION DEVICE

CROSS-REFERENCE TO RELATED APPLICATIONS

This application is a National Stage Application of PCT/US13/70470 under 35 USC § 371 (a), which claims priority of U.S. Provisional Patent Application Ser. No. 61/727,939 filed Nov. 19, 2012, the disclosures of each of the above-identified applications are hereby incorporated by reference in their entirety.

BACKGROUND

Technical Field

The present disclosure relates to medical devices and methods of using the same. More particularly, the present disclosure relates to surgical devices for tissue fixation.

Background of Related Art

Techniques for repairing damaged or diseased tissue are widespread in medicine. Wound closure devices, such as sutures and staples, as well as other repair devices like mesh or patch reinforcements, are frequently used for repair. For example, in the case of hernias, a surgical mesh or patch is commonly used to reinforce the abdominal wall. Typically, sutures, staples, and/or tacks are utilized to fix the surgical mesh or patch to surrounding tissue.

The current standard of care for laparoscopic ventral hernia repair, for example, involves the application of stay sutures that are placed both through a surgical mesh and trans-abdominally, and tied down just underneath the skin. Permanent sutures are typically used for this application. The sutures are placed around the perimeter of the mesh, and sometimes in the center to permanently tie the mesh to the area of herniation and to prevent the mesh from sliding within the peritoneum. For each stay suture, a surgeon will pierce the abdominal wall with a suture passer and grasp one end of a suture that has been pre-placed on the mesh, and pull the end of the suture through the abdominal wall and out past the skin. When the two ends of the suture are outside of the patient, the surgeon will pull up on the mesh and tie down a knot in the suture, compressing the abdominal wall and keeping the mesh tight against the peritoneum. The surgeon will then cut the excess suture and close the skin over the knot. This process may take about a minute or two for each stay suture, and may be associated with acute and/or chronic pain, likely due to compression of the abdominal wall and the nerves within it.

It would be advantageous to provide a fixation device that simplifies and shortens the time to secure a mesh, and limits or prevents pain caused by abdominal wall and nerve compression.

SUMMARY

A tissue fixation device includes an elongated body extending between a proximal portion and a distal portion including a plurality of barbed loops. A first barbed loop may lie substantially in a first plane and a second barbed loop may lie substantially in a second plane. In embodiments, the distal portion further includes a third barbed loop, and in some embodiments, the distal portion also includes a fourth barbed loop. The barbed loops may intersect each other or be separate, and disposed at various orientations with respect to each other. The elongated body, proximal portion, and distal portion are provided in a variety of configurations.

The elongated body may be formed from a single filament or multiple filaments that may each be barbed or unbarbed, and arranged to intersect or remain separate along a length thereof. The filament(s) may be formed from biodegradable and/or non-biodegradable polymeric and/or metallic materials.

The proximal portion may be an extension of the elongated body and terminate in a blunt tip, or may be provided in other configurations, such as a loop. The proximal portion may be free of barbs and a needle. In embodiments, the proximal portion may include a cap. The cap may be magnetic or include a ring extending from a proximal end thereof to aid a clinician in placing the tissue fixation device within tissue. The proximal portion may also include indicia.

The distal portion may include a pledget. The pledget may be disposed at a distalmost end of the distal portion, or may include at least one pair of spaced openings through which a loop of the distal portion may be laced through. The pledget may include a biocompatible coating. In embodiments, the coating is anti-adhesive, and in some embodiments, the coating may include surface reactive functional groups. The pledget may also include barbs and/or darts to mechanically fix the pledget to tissue.

The barbed loops may be fixed to the elongated body, or may be slidable relative thereto. In embodiments, the barbed loops include a distal portion that is fixed to the elongated body and a proximal portion defining an unfixed ring that is translatable along the elongated body. The barbed loops may be configured to move from a first position in which the barbed loops are expanded, and a second position in which the barbed loops are compressed.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

A tissue fixation device and method of using the same are described herein. While the present discussion and figures below depict exemplary embodiments of the present disclosure in terms of a tissue fixation device for use in hernia repair, the presently disclosed devices may be utilized in any surgical procedure requiring joining or positioning of tissue, or fastening of surgical implants thereto.

A tissue fixation device in accordance with the present disclosure includes an elongated body extending between a proximal portion and a distal portion including at least two barbed loops. The tissue fixation device described herein may be formed from any sterilizable biocompatible material that has suitable physical properties for the intended use of the device. The elongated body, distal portion, and/or proximal portion of the tissue fixation device may be fabricated from any biodegradable and/or non-biodegradable polymeric and/or metallic material that can be used in surgical procedures.

The term "biodegradable" as used herein is defined to include both bioabsorbable and bioresorbable materials. By biodegradable, it is meant that the material decomposes, or loses structural integrity under body conditions (e.g., enzymatic degradation or hydrolysis) or is broken down (physically or chemically) under physiologic conditions in the body such that the degradation products are excretable or absorbable by the body. Absorbable materials are absorbed by biological tissues and disappear in vivo at the end of a given period, which can vary, for example, from hours to several months, depending on the chemical nature of the material. It should be understood that such materials include natural, synthetic, bioabsorbable, and/or certain non-absorbable materials, as well as combinations thereof.

Representative natural biodegradable polymers include: polysaccharides such as alginate, dextran, chitin, chitosan, hyaluronic acid, cellulose, collagen, gelatin, fucans, glycosaminoglycans, and chemical derivatives thereof (substitutions and/or additions of chemical groups include, for example, alkyl, alkylene, amine, sulfate, hydroxylations, carboxylations, oxidations, and other modifications routinely made by those skilled in the art); catgut; silk; linen; cotton; and proteins such as albumin, casein, zein, silk, soybean protein, and copolymers and blends thereof; alone or in combination with synthetic polymers.

Synthetically modified natural polymers include cellulose derivatives such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, and cellulose sulfate sodium salt.

Representative synthetic biodegradable polymers include polyhydroxy acids prepared from lactone monomers such as glycolide, lactide, caprolactone, ε-caprolactone, valerolactone, and δ-valerolactone, carbonates (e.g., trimethylene carbonate, tetramethylene carbonate, and the like), dioxanones (e.g., 1,4-dioxanone and p-dioxanone), 1,dioxepanones (e.g., 1,4-dioxepan-2-one and 1,5-dioxepan-2-one), and combinations thereof. Polymers formed therefrom include: polylactides; poly(lactic acid); polyglycolides; poly(glycolic acid); poly(trimethylene carbonate); poly(dioxanone); poly(hydroxybutyric acid); poly(hydroxyvaleric acid); poly(lactide-co-(ε-caprolactone-)); poly(glycolide-co-(ε-caprolactone)); polycarbonates; poly(pseudo amino acids); poly(amino acids); poly(hydroxyalkanoate)s such as polyhydroxybutyrate, polyhydroxyvalerate, poly(3-hydroxybutyrate-co-3-hydroxyvalerate), polyhydroxyoctanoate, and polyhydroxyhexanoate; polyalkylene oxalates; polyoxaesters; polyanhydrides; polyester anyhydrides; poly-ortho esters; and copolymers, block copolymers, homopolymers, blends, and combinations thereof.

Some non-limiting examples of suitable non-degradable materials include: polyolefins such as polyethylene (including ultra high molecular weight polyethylene) and polypropylene including atactic, isotactic, syndiotactic, and blends thereof; polyethylene glycols; polyethylene oxides; polyisobutylene and ethylene-alpha olefin copolymers; fluorinated polyolefins such as fluoroethylenes, fluoropropylenes, fluoroPEGSs, and polytetrafluoroethylene; polyamides such as nylon, Nylon 6, Nylon 6,6, Nylon 6,10, Nylon 11, Nylon 12, and polycaprolactam; polyamines; polyimines; polyesters such as polyethylene terephthalate, polyethylene naphthalate, polytrimethylene terephthalate, and polybutylene terephthalate; polyethers; polybutester; polytetramethylene ether glycol; 1,4-butanediol; polyurethanes; acrylic polymers; methacrylics; vinyl halide polymers such as polyvinyl chloride; polyvinyl alcohols; polyvinyl ethers such as polyvinyl methyl ether; polyvinylidene halides such as polyvinylidene fluoride and polyvinylidene chloride; polychlorofluoroethylene; polyacrylonitrile; polyaryletherketones; polyvinyl ketones; polyvinyl aromatics such as polystyrene; polyvinyl esters such as polyvinyl acetate; etheylene-methyl methacrylate copolymers; acrylonitrile-styrene copolymers; ABS resins; ethylene-vinyl acetate copolymers; alkyd resins; polycarbonates; polyoxymethylenes; polyphosphazine; polyimides; epoxy resins; aramids; rayon; rayon-triacetate; spandex; silicones; and copolymers and combinations thereof.

In embodiments, the elongated body, distal portion, proximal portion, or portions thereof may be formed from polybutester, a copolymer of butylenes terephthalate and polytetramethylene ether glycol. For example, the tissue fixation device, or portions thereof, may be formed from the commercially available nonabsorbable polybutester monofilaments, sold under the trade name Novafil™ by Covidien. In some embodiment, the tissue fixation device, or portions thereof, may be formed from a copolymer of glycolic acid and trimethylene carbonate, such as, for example, Maxon™, commercially available from Covidien. In embodiments, the tissue fixation device, or portions thereof, may be formed from a terpolymer of glycolic acid, trimethylene carbonate, and dioxanone, such as, for example, Biosyn™, commercially available from Covidien.

In embodiments, the tissue fixation device may include: metals such as steel or titanium; metal alloys including degradable alloys such as iron-based or magnesium-based degradable alloys; and the like.

The elongated body of the tissue fixation device described herein may be formed from monofilament or multi-filament structures that are fabricated from natural, synthetic, degradable, and/or non-degradable materials, as well as combinations thereof, as described above. The elongated body may be formed using any technique within the purview of those skilled in the art such as, for example, extrusion, molding, casting, and/or spinning. Where the elongated body is made of multiple filaments, the elongate body may be formed using any known technique such as, for example, braiding, weaving or knitting. The filaments may also be drawn, oriented, annealed, calendared, crinkled, twisted, commingled, or air entangled to form the elongated body.

In embodiments, the elongated body, or portions thereof, may be barbed. The barbs may be single or compound barbs formed along a portion or the entire length of the elongated body in specified or random patterns. Barbs may be formed from angled cuts in an outer surface of the elongated body, or barbs may be molded on the outer surface of the elongated body, such that an inner surface of the barb is positioned opposite to an outer surface of the elongated body. The barbs may all be oriented in the same or different directions, and may be cut at the same or different barb angles. Compound barbs include an inner surface including at least two angled cuts disposed at first and second orientations, respectively, relative to a longitudinal axis of the elongated body. Examples of compound barbs which may be utilized include those disclosed in U.S. Patent Application Publication No. 2009/0210006, entitled "Compound Barb Medical Device and Method", the entire disclosure of which is incorporated by reference herein.

The surface area of the barbs may vary. For example, fuller-tipped barbs can be made of varying sizes designed for specific surgical applications. When joining fat and relatively soft tissues, large barbs may be desired, whereas smaller barbs may be more suitable for collagen-dense tissues. In some embodiments, a combination of large and small barbs on the same structure may be beneficial, for example, when used in a tissue repair with differing tissue layer structures. A combination of large and small barbs may be used within the same tissue fixation device such that the barb sizes are customized for each tissue layer to ensure maximum holding properties.

The distal portion includes a plurality of barbed loops. The barbed loops may be permanently or releasably secured to the elongated body by convention means, such as, for example, ultrasonic welding or with the use of adhesives, or may be integrally formed with the elongated body. Similarly, the proximal portion may be a component separate from, and joined to, the elongated body, or monolithically formed with the elongated body. The distal and/or proximal portions may be formed from the same or different materials than that of the elongated body.

Referring now to the drawings, FIG. 1 illustrates a tissue fixation device 100 of the present disclosure. Tissue fixation device 100 includes an elongated body 110, a proximal portion 120, and a distal portion 130. The elongated body 110 extends between the proximal portion 120 and the distal portion 130, and is illustrated as a solid structure that is free of barbs. Although shown as having a substantially circular cross-sectional geometry, the elongated body portion may be any suitable shape, such as round, elliptical, square, flat, octagonal, and rectangular, among other geometric and non-geometric shapes. In embodiments, the elongated body 110 may have a varying diameter, e.g., the elongated body may have a smaller diameter at a proximal end that gradually transitions to a larger diameter at a distal end.

Proximal portion 120 contiguously extends from the elongated body 110 and may terminate in a blunt tip 122. Distal portion 130 includes at least two loops 132, each loop 132 having first and second segments 132a and 132b interconnected by a terminal end portion 132c. Barbs 134 may be disposed on any portion of a loop 132, in embodiments, barbs 134 are disposed on at least the portion of a loop 132 closest to the elongated body 110. As illustrated, barbs 134 are disposed on the first and second segments 132a and 132b of the loops 132, while the terminal end portion 132c is free of barbs.

Figure 1A:
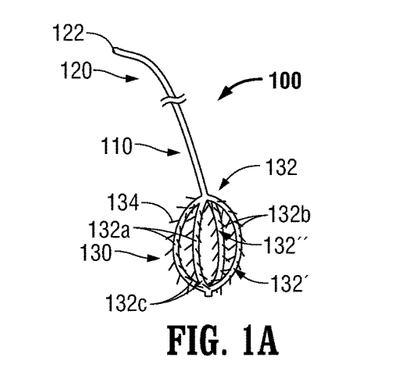
FIG. 1A is a side view of a tissue fixation device in accordance with an embodiment of the present disclosure.
Figure 1B:
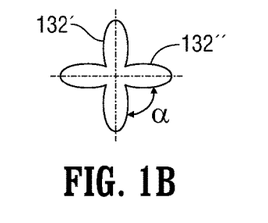
FIG. 1B is a bottom view of the tissue fixation device of FIG. 1A.
Figure 1C:
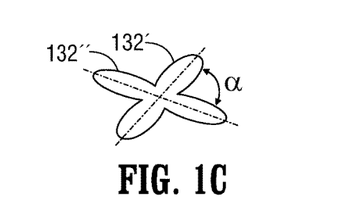
FIGS. 1C and 1D are bottom views of tissue fixation devices in accordance with other embodiment of the present disclosure.
Figure 1D:
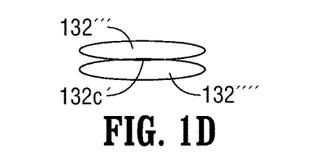

The distal portion 130 includes a first loop 132' lying substantially in a first plane and a second loop 132" lying substantially in a second plane that is different from the first plane. While the first and second loops 132' and 132" are illustrated as being substantially orthogonal to each other (FIG. 1B) such that the first and second planes intersect at an angle α of about 90°, it should be understood that the first and second loops may intersect or extend separately from the elongated body 110 at any orientation with respect to each other. Angle α may be any angle between 0° to 90°, such as an acute angle of about 30°, as illustrated in FIG. 1C. In embodiments, angle α may be about 0° such that the first and second loops 132''' and 132'''' lie in substantially parallel planes as illustrated in FIG. 1D. First and second loops 132''' and 132'''' may be interconnected at terminal end portion 132c' by bonding first and second loops 132''' and 132'''' together.

The distal portion of the tissue fixation device may be provided with a pledget, such as those shown in FIGS. 2A-2E. A pledget may be formed from plastic, polymeric, or other biocompatible materials, including non-degradable and/or degradable materials as described above. For example, in embodiments in which the distal portion of the tissue fixation device is fabricated from a non-degradable material, a non-degradable pledget may be utilized, such as a pledget fabricated from a silicone or fluorocarbon based material, like polytetrafluoroethylene (e.g., TEFLON). Similarly, in some embodiments in which the distal portion of the tissue fixation device is fabricated from a biodegradable material, a biodegradable pledget may be utilized, such as a pledget fabricated from a copolymer of lactide and glycolide.

In embodiments, a pledget may include magnetic material to aid a clinician in positioning the pledget against tissue with the use of an external magnet. A pledget may be fabricated from an absorbable and/or non-absorbable magnet material, such as a ferromagnetic metal. Suitable metals include iron ore (magnetite or lodestone), cobalt and nickel, rare earth metals like gadolinium and dysprosium, and alloys thereof. The pledget may also be made from composite materials such as ceramic or ferrite, alnico (a combination of aluminum, nickel and cobalt with iron), or triconal (a combination of titanium, cobalt, nickel and aluminum with iron). In some embodiments, a pledget may be formed from a polymeric material including ferromagnetic metal particles. The polymer may be any biodegradable and/or non-biodegradable polymer as described above. In embodiments, ferromagnetic metal particles may be freely admixed or co-extruded with the polymer forming the pledget, or may be tethered to the polymer through any suitable chemical bond. In some embodiments, the ferromagnetic metal particles may be spray or dip coated on a formed pledget.

Figures 2A, 2B:
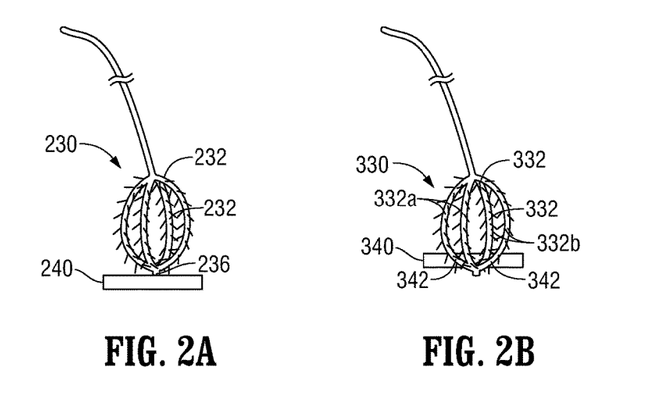
FIGS. 2A-2E are side views of various embodiments of a distal portion of a tissue fixation device of the present disclosure.

A pledget 240 may be securely fastened to a distalmost end 236 of at least one of the loops 232, as illustrated in FIG. 2A, or may include openings 342 that are dimensioned to allow passage of the first and second segments 332a and 332b of at least one of the loops 332 therethrough so that the pledget 340 may be positioned along any portion of the distal portion 330, as illustrated in FIG. 2B.

In embodiments, a pledget may include a coating. The coating may be utilized to alter the physical properties on the surface of the pledget (e.g., enhance lubricity), or may provide a therapeutic benefit to tissue. In general, a coating may be applied to a surface of the pledget, or selective regions thereof, by, for example, spraying, dipping, brushing, vapor deposition, co-extrusion, capillary wicking, film casting, molding, etc.

Therapeutic agents include any substance or mixture of substances that have clinical use. Alternatively, a therapeutic agent could be any agent which provides a therapeutic or prophylactic effect; a compound that affects or participates in tissue growth, cell growth and/or cell differentiation; a compound that may be able to invoke or prevent a biological action such as an immune response; or a compound that could play any other role in one or more biological processes. A variety of therapeutic agents may be coated on a pledget, or incorporated into the tissue fixation device of the present disclosure. Moreover, any agent which may enhance tissue repair, limit the risk of sepsis, and modulate the mechanical properties of the tissue fixation device (e.g., the swelling rate in water, tensile strength, etc.) may be added to the material forming the tissue fixation device or may be coated thereon.

Examples of classes of therapeutic agents which may be utilized in accordance with the present disclosure include antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of therapeutic agents may be used.

Other therapeutic agents which may be in the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable therapeutic agents which may be included in the present disclosure include: viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons (β-IFN, (α-IFN and γ-IFN)); erythropoietin; nucleases; tumor necrosis factor; colony stimulating factors (e.g., GCSF, GM-CSF, MCSF); insulin; anti-tumor agents and tumor suppressors; blood proteins; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); protein inhibitors; protein antagonists; protein agonists; nucleic acids such as antisense molecules, DNA, and RNA; oligonucleotides; and ribozymes.

Figure 2C:
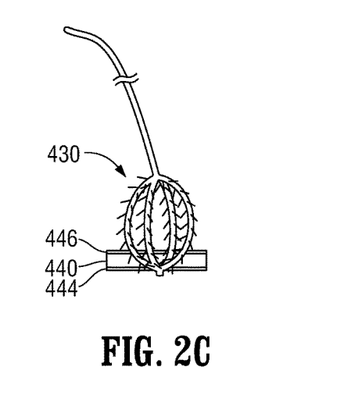

As illustrated in FIG. 2C, a bottom surface 444 of a pledget 440 may include an anti-adhesive coating that acts as a barrier layer between the tissue fixation device and surrounding tissue to prevent the formation of adhesions, and a top surface 446 of the pledget 440 may be surface treated in order to promote adhesion to tissue. In embodiments, the top surface 446 may include a coating containing tissue reactive functional groups for fixation of the pledget 440 to tissue by crosslinking with reactive groups present in tissue such as primary amine groups, secondary amine groups, hydroxyl groups, carboxylic groups, sulfonic groups, combinations thereof, and the like. Such groups include compounds possessing chemistries having some affinity for tissue.

Figure 2D:
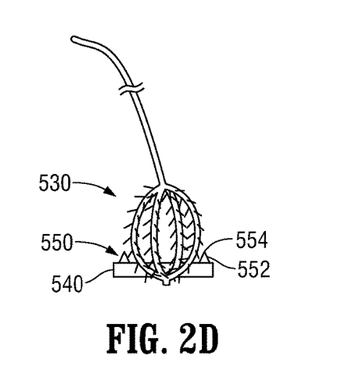
Figure 2E:
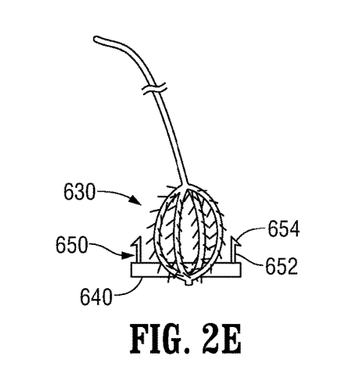

FIGS. 2D and 2E illustrate a distal portion including a pledget having mechanical means of attachment to tissue. The pledget may include mechanical barbs, grips, hooks, or darts to achieve, or enhance, adhesivity to tissue. As illustrated in FIG. 2D, a pledget 540 may include a mechanical dart 550 including a base portion 552 tapering toward a sharp tip 554. The base portion 552 includes a larger diameter than the tip 554 for enhanced tissue fixation. As illustrated in FIG. 2E, pledge 640 may including mechanical darts 650, each dart 650 including an arm 652 having a sharp or pointed tip 654 for piercing and gripping tissue.

Figure 3A:
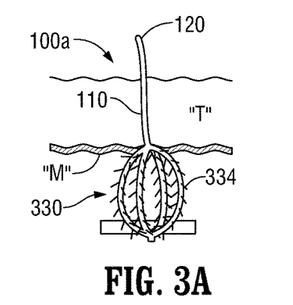
FIGS. 3A-3C are schematic illustrations of an exemplary method of using a tissue fixation device of the present disclosure.
Figure 3B:
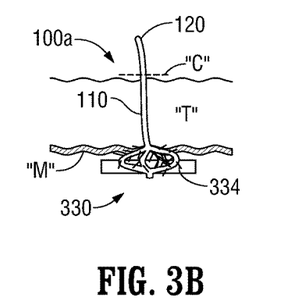
Figure 3C:
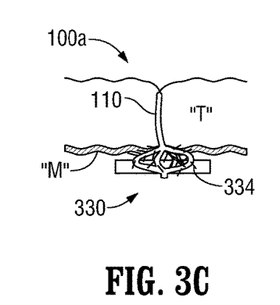

FIGS. 3A-3C illustrate an exemplary method for fixing a hernia mesh "M" to tissue "T" with a tissue fixation device of the present disclosure. As illustrated in FIG. 3A, tissue fixation device 100a is delivered to a surgical site and positioned with the elongated body 110 and proximal portion 120 extending through the tissue "T", and the distal portion 330 (FIG. 2B) abutting hernia mesh "M". The tissue fixation device 100a may be delivered to the surgical site using a conventional suturing device, such as an Endo Close™ Single Use Suturing Device, commercially available from Covidien. For example, the tissue fixation device 100a may be hooked through a portion of a stylet of the Endo Close™ device and drawn within the cannula of the device. The Endo Close™ device may then be inserted through the tissue and released under the fascia without the need for a sharp piercing tip on the proximal portion of the tissue fixation device.

After the tissue fixation device 100a is delivered through the tissue "T", a clinician may pull up on the proximal portion 120 of the tissue fixation device 100a such that the distal portion 330 is compressed against the hernia mesh "M" and tissue "T", as illustrated in FIG. 3B. The barbs 334 located on the distal portion 330 of the tissue fixation device 300 adhere to the hernia mesh "M" and/or tissue "T", fixing the distal portion 330 thereagainst. The clinician may then cut the proximal portion 120, or a portion of the elongated body 110, for example, along cut line "C", allowing the tissue fixation device 100a to hold the hernia mesh "M" against tissue "T", as illustrated in FIG. 3C, without compressing the tissue "T" with a suture knot, as required by traditional devices. In embodiments, the proximal portion 120 may be formed from a biodegradable material and the distal portion 330 may be formed from a non-degradable material to aid in patient comfort by limiting the mass of the tissue fixation device within the tissue while retaining fixation integrity of the hernia mesh "M".

Figure 4:
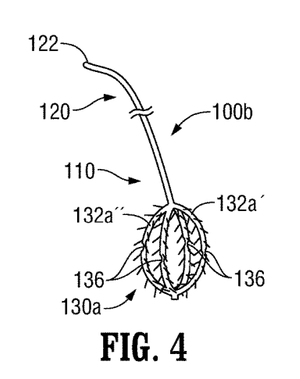
FIG. 4 is a side view of a tissue fixation device in accordance with another embodiment of the present disclosure.

At least one barbed loop of a tissue fixation device may, alternatively or additionally, include sections of reduced diameter to account for bending moments in the distal portion during use. For example, as illustrated in FIG. 4, tissue fixation device 100b includes a distal portion 130a in which first and second loops 132a' and 132a" includes notches 136 in a surface thereof to increase flexibility of the loop.

Figure 5A:
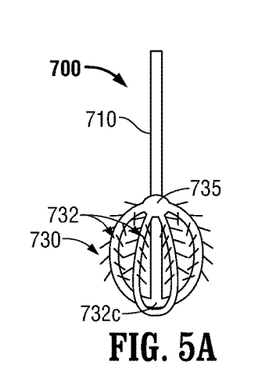
FIGS. 5A and 5B are side views of a tissue fixation device in accordance with yet another embodiment of the present disclosure.
Figure 5B:
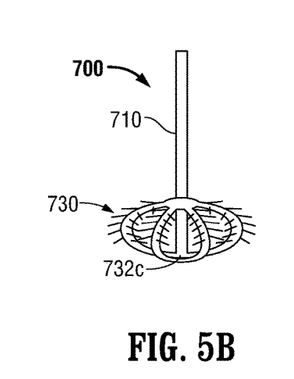

With reference now to FIGS. 5A and 5B, the size of the barbed loops of a tissue fixation device in accordance with the present disclosure may be adjustable. Tissue fixation device 700 is substantially similar to tissue fixation device 100 and will therefore only be described as related to differences therebetween. Tissue fixation device 700 includes a distal portion 730 that is slidably disposed along elongated body 710. The distal portion 730 is configured to include at least two loops 732 that intersect at the terminal distal end 732c of each loop 732, the terminal distal ends 732 being contiguous with a terminal end of the elongated body 710. The first and second segments 732a and 732b of the loops 732 are joined at a proximal end to form an unattached ring 735 that is translatable along the elongated body 710. The loops 732 are configured to move from a first position in which the loops are expanded, as shown in FIG. 5A, and a second position in which the loops are compressed, as illustrated in FIG. 5B. Accordingly, as a clinician pulls up on the tissue fixation device 700, once placed in tissue, the ring 735 slides down the elongated body 710 and into the compressed configuration of FIG. 5B.

Figure 6:
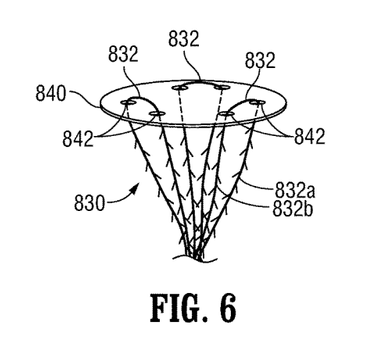
FIGS. 6 and 7 are perspective views of embodiments of a distal portion of a tissue fixation device of the present disclosure.
Figure 7:
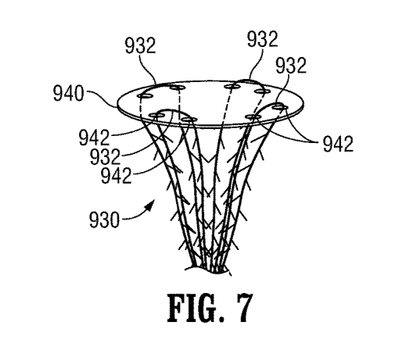

Referring now to FIG. 6, a distal portion 830 of a tissue fixation device may include three loops 832. A pledget 840 may be associated with the distal portion 840 and include a plurality of paired openings 842 disposed in spaced relation about the pledget 840. Each paired opening 842 is configured to receive segments 832a and 832b of a loop 832 so that the loop 832 may be laced therethrough. The tissue fixation device of FIG. 7 is similar to tissue fixation device of FIG. 6, except that the distal portion 930 of the tissue fixation device includes four loops 932. As illustrated in FIG. 7, a pledge 940 includes a plurality of paired openings 942 that are radially disposed around the pledget 940 so that the distal portion 940 tapers from the pledget 940 towards the elongated body (not shown).

Figure 8A:
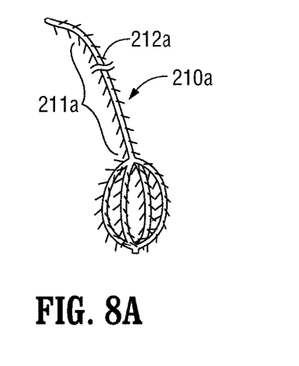
FIGS. 8A-8K are side views of various embodiments of body sections of a tissue fixation device of the present disclosure.
Figure 8B:
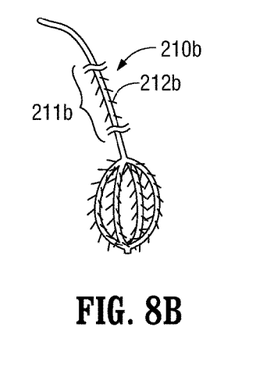
Figure 8C:
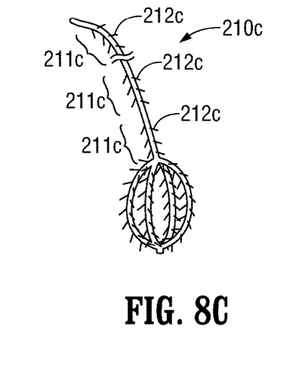

The elongated body of the tissue fixation device of the present disclosure may be provided in a variety of configurations. The elongated body may include body sections having a structure, such as barbs and/or multi-filaments segments, that is different from that of the monofilament structure of FIG. 1. The body sections may extend along the entire length of the elongated body, or along portion(s) thereof. For example, as illustrated in FIG. 8A, an elongated body 210a may include a body section 211a including barbs 212a extending along the entire length thereof to aid in fixing the tissue fixation device within tissue. In some embodiments, as illustrated in FIG. 8B, a body section 211b including barbs 212b may be provided on only a select portion of the elongated body 210b. And in other embodiments, as illustrated in FIG. 8C, a body section 211c including barbs 212c may be provided in spaced intervals along the length of the elongated body 210c. As described above with respect to the barbs of the distal portion of the tissue fixation device, the barbs of the elongated body may also be provided with any barb configuration (e.g., single or compound), in any pattern thereon.

Figure 8D:
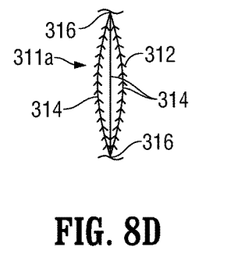
Figures 8E, 8F:
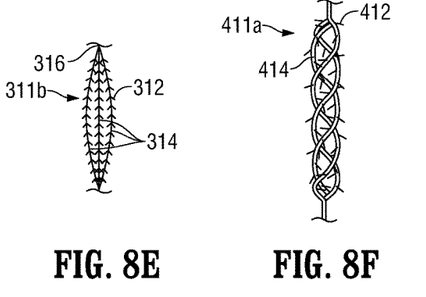

FIGS. 8D-8K illustrate exemplary embodiments of other body sections that may be incorporated into an elongated body of the present disclosure. As illustrated in FIG. 8D, for example, a body section 311a may include a combination of barbed and unbarbed filaments 314 that are substantially separate and in spaced relation to each other along a majority of the length thereof, and united only at pre-defined points 316 positioned at opposed terminal ends of the body section 311a. The filaments 314 may be bonded, welded, fused, knotted, braided, twisted, entangled, or otherwise joined at the pre-defined points 316. FIG. 8E differs from FIG. 8D in that all of the filaments 314 of the elongated body 310b in FIG. 8E include barbs 312.

Figure 8G:
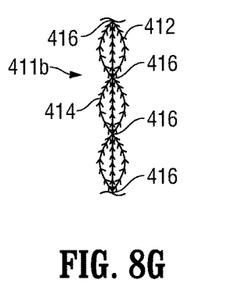
Figure 8H:
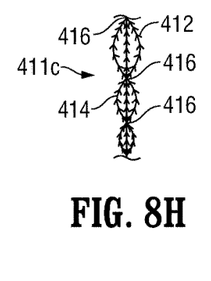

Alternatively, as illustrated in FIGS. 8F-8K, filaments may be commingled along the length of a body section. FIG. 8F illustrates a body section 411a including a plurality of filaments 414 each including barbs 412 in a braided configuration. FIG. 8G illustrates a body section 411b including a plurality of filaments 414 that intersect at least one other filament at pre-defined points 416 along the length of the body section 411b. As shown, all filaments 414 intersect at pre-defined points 416 that are substantially evenly spaced along the length of the body section 411b. In other embodiments, the pre-defined points may be unevenly spaced along the length of the body section. As shown in FIG. 8H, for example, varying the spacing between pre-defined points 416 may provide the body section 411c with a tapered or varied shape along the length thereof.

Figure 8I:
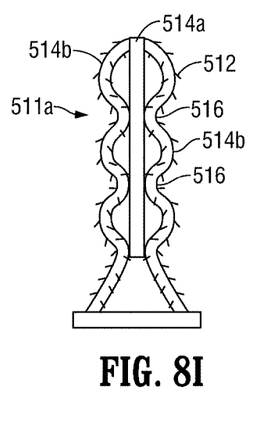
Figure 8J:
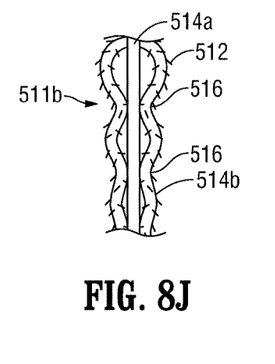

FIG. 8I illustrates a body section 511a including a plurality of filaments 514 including a central filament 514a and at least one outer filament 514b. The outer filament 514b is joined to the central filament 514a at pre-defined points 516 therealong, such as by fusing the central filament 514a and the outer filament 514b together. The central filament 514a is illustrated as being free of barbs and the outer filaments 514b as including barbs 512. In embodiments, the central filament 514a may be formed from a non-absorbable material and the outer filaments 514b may be formed from an absorbable material. In some embodiments, the central filament 514a may have a larger diameter than the outer filaments 514b. In other embodiments, as illustrated in FIG. 8J, the shape of the body section 511b may be varied by varying the length of the outer filaments 514b provided between the pre-defined points 516.

Figure 8K:
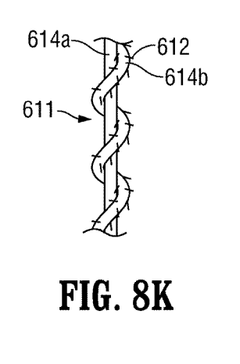

FIG. 8K illustrates a body section 611 including a central filament 614a and an outer filament 614b twisted around the central filament 614a. As illustrated, the central filament 614 is free of barbs and the outer filament 614b includes barbs 612, however, it is envisioned that any barbed/unbarbed configuration of filaments may be utilized. It should be understood that the body section may include any number of barbed and/or unbarbed filaments that are gathered in a variety of configurations. The filaments may all be fabricated from the same or different materials, and be of the same or different cross-sectional diameter or size.

Figure 9A:
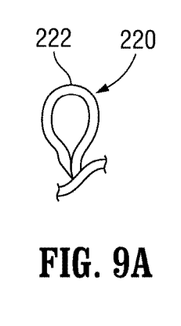
FIGS. 9A-9E are side view of various embodiments of a proximal portion of a tissue fixation device of the present disclosure.
Figure 9B:
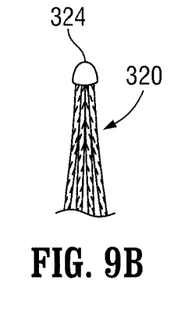

Referring again to FIG. 1, the proximal portion 120 is illustrated as a longitudinally extending segment terminating in an unsharpened tip 122. The proximal portion of the tissue fixation device may also be provided in a variety of other configurations having a blunted tip, such as that shown in FIG. 9A. As illustrated in FIG. 9A, a proximal portion 220 may be formed into a loop 222. As illustrated in FIG. 9B, a proximal portion 320 may terminate in a cap 324. The cap may be formed from any polymeric and/or metallic material as described above, and in embodiments in which the elongated body is formed from a plurality of filaments, may be utilized to gather and crimp the filament together at a terminal end thereof.

Figure 9C:
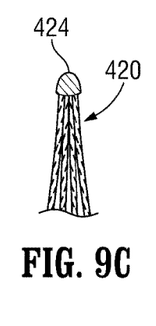

In embodiments, as illustrated in FIG. 9C, the cap 424 may be formed from a magnetic material, such as those described above in reference to the pledget of the distal portion.

Figure 9D:
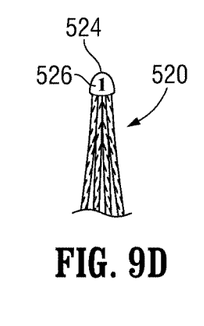

In embodiments, the cap may include indicia, such as shapes, symbols, numerals, text, among other markings, for identifying the proximal portion of the tissue fixation device. FIG. 9D illustrates a proximal portion 520 including a cap 524 including indicia 526. The indicia may be in any shape and size to provide a visibly distinguishable mark or pattern on the proximal portion of the tissue fixation device. In embodiments, indicia may be applied by utilizing ink that may be visualized under visible, infrared, ultraviolet, and/or by other wavelengths of light. In some embodiments, dyes may be utilized. Dyes include, but are not limited to, carbon black, bone black, FD&C Blue #1, FD&C Blue #2, FD&C Blue #3, FD&C Blue #6, D&C Green #6, D&C Violet #2, methylene blue, indocyanine green, other colored dyes, and combinations thereof. It is envisioned that visualization agents may also be used, such as fluorescent compounds (e.g., fluorescein or eosin), x-ray contrast agents (e.g., iodinated compounds), ultrasonic contrast agents, and MRI contrast agents (e.g., Gadolinium containing compounds). A variety of applicators within the purview of those skilled in the art may be used to apply the indicia, including, for example, syringes, droppers, markers or pen-like applicators, brushes, sponges, patches, combinations thereof, and the like.

Figure 9E:
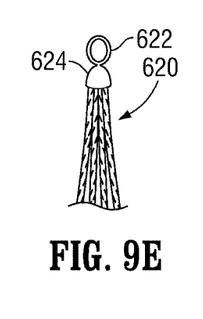

FIG. 9E illustrates a proximal portion 620 including a cap 624 having a ring 622 extending proximally therefrom. A ring 622 may be utilized to aid a clinician in pulling a tissue fixation device up through tissue, as described above with respect to the exemplary method of using a tissue fixation device as described above.

Persons skilled in the art will understand that the devices and methods specifically described herein, and illustrated in the accompanying drawings, are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosed devices and methods based on the above-described embodiments. As such, further modifications and equivalents of the invention herein disclosed can occur to persons skilled in the art using no more than routine experimentation, and all such modifications and equivalents are believed to be within the spirit and scope of the disclosure as defined by the following claims.

What is claimed is:

1. A tissue fixation device comprising a proximal portion including an elongated body that is a monofilament structure formed from one filament having a distal end and a proximal end, and a distal portion including first and second barbed loops, each of the first and second barbed loops extending distally and contiguously, in touching relation, from a distal-most end of the one filament forming the elongated body, the first barbed loop lying substantially in a first plane and the second barbed loop lying substantially in a second plane, a distal-most end of at least one of the first or second barbed loops defining a distal-most end of the tissue fixation device.

2. The tissue fixation device of claim 1, wherein the first plane of the first barbed loop is substantially orthogonal to the second plane of the second barbed loop.

3. The tissue fixation device of claim 1, wherein the proximal end is free of barbs and terminates in a blunt tip.

4. The tissue fixation device of claim 1, wherein the proximal end of the one filament of the elongated body is formed into a loop.

5. The tissue fixation device of claim 4, wherein a terminal end of the one filament of the elongate body is joined to a portion of the one filament distal to the terminal end to form the loop and define an opening therethrough.

6. The tissue fixation device of claim 4, wherein the loop of the proximal end is free of barbs.

7. The tissue fixation device of claim 1, wherein the proximal portion includes a cap.

8. The tissue fixation device of claim 7, wherein the cap is magnetic.

9. The tissue fixation device of claim 1, wherein the distal portion includes a pledget.

10. The tissue fixation device of claim 9, wherein the pledget includes a proximal surface and a distal surface, the proximal surface including at least one dart extending proximally therefrom.

11. The tissue fixation device of claim 9, wherein the pledget is disposed at a distal-most end of at least one of the first and second barbed loops.

12. The tissue fixation device of claim 9, wherein the pledget includes at least one pair of spaced openings, and at least one of the first and second barbed loops is laced through the openings.

13. The tissue fixation device of claim 1, wherein the distal portion includes a third barbed loop.

14. The tissue fixation device of claim 13, further comprising a pledget including a plurality of paired openings disposed in spaced relation relative to each other, each of the paired openings configured to receive one of the barbed loops.

15. The tissue fixation device of claim 13, wherein the distal portion further comprises a fourth barbed loop.

16. The tissue fixation device of claim 15, further comprising a pledget including a plurality of paired openings disposed radially therearound, each of the paired openings configured to receive one of the barbed loops.

17. The tissue fixation device of claim 1, wherein the first and second barbed loops are configured to move from a first position in which the first and second barbed loops are expanded and a second position in which the first and second barbed loops are compressed.

18. The tissue fixation device of claim 1, wherein the elongated body includes barbs.

19. The tissue fixation device of claim 1, wherein each of the first and second barbed loops has a continuous closed body beginning and ending at the distal-most end of the elongate body, and the distal-most end of each of the first and second barbed loops is free of barbs.

20. The tissue fixation device of claim 1, wherein the distal-most ends of the first and second barbed loops are coterminous.

* * * * *